US011794769B2

(12) United States Patent
Gossele et al.

(10) Patent No.: US 11,794,769 B2
(45) Date of Patent: Oct. 24, 2023

(54) DETERMINATION OF A STATE OF A USER ACTIVELY DRIVING A MOTOR VEHICLE OR NOT

(71) Applicant: VALEO VISION, Bobigny (FR)

(72) Inventors: Frederic Gossele, Bobigny (FR); Pierre Cesar Lafaysse, Bobigny (FR); Pierre Louis Thouvenot, Bobigny (FR)

(73) Assignee: Valeo Vision, Bobigny (FR)

(*) Notice: Subject to any disclaimer, the term of this patent is extended or adjusted under 35 U.S.C. 154(b) by 33 days.

(21) Appl. No.: 17/764,411

(22) PCT Filed: Sep. 25, 2020

(86) PCT No.: PCT/EP2020/077010
§ 371 (c)(1),
(2) Date: Mar. 28, 2022

(87) PCT Pub. No.: WO2021/063846
PCT Pub. Date: Apr. 8, 2021

(65) Prior Publication Data
US 2022/0332340 A1 Oct. 20, 2022

(30) Foreign Application Priority Data
Oct. 3, 2019 (FR) ...................................... 1910976

(51) Int. Cl.
G08B 23/00 (2006.01)
B60W 50/14 (2020.01)
(Continued)

(52) U.S. Cl.
CPC .......... B60W 50/14 (2013.01); B60W 30/146 (2013.01); B60W 40/08 (2013.01);
(Continued)

(58) Field of Classification Search
CPC .... B60W 50/14; B60W 30/146; B60W 40/08; B60W 50/0098; B60W 2540/01;
(Continued)

(56) References Cited

U.S. PATENT DOCUMENTS

2009/0201309 A1* 8/2009 Demos ...................... G09G 5/02
345/589
2014/0152792 A1* 6/2014 Krueger ............... A61B 5/4863
348/78
2015/0293586 A1* 10/2015 Kritt ....................... G06F 3/013
345/158

FOREIGN PATENT DOCUMENTS

DE 02015011708 A1 5/2016
EP 2952403 A2 12/2015
(Continued)

OTHER PUBLICATIONS

European Patent Office, International Search Report (w/English translation) and Written Opinion of corresponding Application No. PCT/EP2020/077010, dated Nov. 11, 2020.

Primary Examiner — Naomi J Small
(74) Attorney, Agent, or Firm — Valeo Vision

(57) ABSTRACT

A method and device for determining whether a user is actively driving a motor vehicle or car sick. The sensor device is provided for sensing eye movement of the user and the method includes supplying an artificial intelligence with data originating from the sensor device in order to recognize at least one frequency of eye movements of the user, a frequency of eye movements above a first threshold characterizing a visualization by the user of a passing landscape, and being distinguished from a concentration of gaze of a vehicle driver, and determining a current frequency of eye movements of the user and comparing the current frequency (Continued)

with the first threshold, and if the current frequency is greater than the first threshold, triggering a notification signal for the user.

15 Claims, 3 Drawing Sheets

(51) Int. Cl.
| | |
|---|---|
| *H04W 4/90* | (2018.01) |
| *H04W 4/40* | (2018.01) |
| *G06V 10/82* | (2022.01) |
| *G06V 20/59* | (2022.01) |
| *G06V 40/19* | (2022.01) |
| *B60W 30/14* | (2006.01) |
| *B60W 40/08* | (2012.01) |
| *B60W 50/00* | (2006.01) |
| *G02B 27/00* | (2006.01) |
| *G02B 27/01* | (2006.01) |
| *G06F 3/01* | (2006.01) |
| *H04W 4/021* | (2018.01) |

(52) U.S. Cl.
CPC ..... *B60W 50/0098* (2013.01); *G02B 27/0093* (2013.01); *G02B 27/017* (2013.01); *G06F 3/013* (2013.01); *G06V 10/82* (2022.01); *G06V 20/597* (2022.01); *G06V 40/19* (2022.01); *H04W 4/021* (2013.01); *H04W 4/40* (2018.02); *H04W 4/90* (2018.02); *B60W 2040/0818* (2013.01); *B60W 2540/01* (2020.02); *B60W 2540/225* (2020.02); *B60W 2540/229* (2020.02); *B60W 2556/50* (2020.02)

(58) Field of Classification Search
CPC ....... B60W 2556/50; B60W 2540/225; B60W 2540/229; B60W 2040/0818; H04W 4/90; H04W 4/40; H04W 4/021; G06V 10/82; G06V 20/597; G06V 40/19; G02B 27/0093; G02B 27/017; G06F 3/013
USPC ........................................................ 340/576
See application file for complete search history.

(56) References Cited

FOREIGN PATENT DOCUMENTS

| | | |
|---|---|---|
| KR | 20180072523 A | 6/2018 |
| WO | 2017192260 A1 | 11/2017 |
| WO | 2017195200 A2 | 11/2017 |

* cited by examiner

DETERMINATION OF A STATE OF A USER ACTIVELY DRIVING A MOTOR VEHICLE OR NOT

CROSS-REFERENCE TO RELATED APPLICATIONS

This application is filed under 35 U.S.C. § 371 U.S. National Phase of International Application No. PCT/EP2020/077010 filed Sep. 25, 2020 (published as WO202163846), which claims priority benefit to French application No. 1910976 filed on Oct. 3, 2019, the disclosures of which are herein incorporated by reference in their entirety.

TECHNICAL FIELD

The present invention relates to the determination of at least one state of a user in a motor-vehicle passenger compartment, regarding whether a user is actively driving the vehicle or not.

What is meant by "person not actively driving the vehicle" is equally well:
- a passenger in the vehicle (who is not the driver),
- as a driver of an autonomous vehicle, the vehicle being autonomous above a threshold (80% for example).

BACKGROUND OF THE INVENTION

A major cause of road accidents is related to the use of telecommunication apparatuses (smartphones, etc.). In particular, on reception of notifications, the user is tempted to focus the user's attention on the screen of the user's smartphone. One way of remedying this problem is to detect that the user is in a moving vehicle (for example using a geolocation module in the telecommunications device) and to filter all incoming communications intended for the user's device. However, this is an extreme solution because a user may simply be a passenger in the vehicle. Furthermore, with the proliferation of autonomous vehicles, drivers are increasingly available to receive notifications on their smartphones if they are not actively driving their vehicle.

More generally, the present disclosure thus aims to detect whether the current state of a user is one of actively driving, or not, a vehicle. For example, it may then be possible to transmit notifications to the user if the user is detected to not be actively driving the vehicle. To this end, the present disclosure proposes to follow the eye movements of the user (via a camera typically employing eye tracking). Specifically, it has been observed that a user who is a passenger or who is simply not actively driving the vehicle has a tendency to direct the user's gaze toward the landscape outside the user's window, which the user watches pass by. On the contrary, a user actively driving the vehicle focuses the user's attention on the road and the user's gaze is more fixed. Thus the frequency of redirection of the gaze may be used as a criterion to determine, if it is typically above a threshold, that a user is not an active driver.

Nevertheless, it has been observed that the frequency of redirection of the gaze may be specific to a user, and that it may vary from one user to the next.

BRIEF SUMMARY OF THE INVENTION

The present disclosure improves the situation.

To this end, it provides a method for determining at least one state of a user in a motor-vehicle passenger compartment, regarding whether the user is actively driving the vehicle or not, wherein a device for sensing eye movements of the user is provided. In particular, the method includes feeding an artificial intelligence with data generated by the sensor device with a view to recognizing at least one eye-movement frequency of the user, an eye-movement frequency above a first threshold being characteristic of the user viewing a landscape passing by, and being distinguishable from the concentrated gaze of a vehicle driver, determining a current eye-movement frequency of the user and comparing the current frequency with the first threshold, and if the current frequency is higher than the first threshold, triggering a notification signal intended for the user.

Thus, the use of artificial intelligence makes it possible to determine, via machine learning and with certainty, for a given user, whether the user is actually in an active driving state or not, by measuring the user's average or habitual eye-movement frequency when not in an active driving state. More precisely, this eye-movement frequency may vary with the speed of the vehicle and be calibrated as a function of speed for a specific given user to the behavior of whom a prior step of learning will have been applied with a view to feeding the aforementioned artificial intelligence.

Such an embodiment thus makes it possible to determine in a precise and certain manner whether the user is actively driving or not, this having many advantages including on the one hand, it is possible to avoid the display of notifications on a communication device of the user when the latter is detected to be actively driving the vehicle, even if the vehicle is not moving at high speed, and on the other hand, it is possible to let received notifications be displayed on the communication device of the user when the latter is detected to not be actively driving the vehicle.

By "gaze concentration of the vehicle driver", what is meant is the gaze concentration, typically on the road, that a vehicle driver habitually applies.

Moreover, and as indicated above, what is meant by "user not actively driving the vehicle" is equally well a passenger of the vehicle who is not the driver, as a driver of a vehicle that is autonomous above a threshold (situation in which autonomy is above 80% for example).

Thus, in one embodiment, if the aforementioned current frequency is higher than the first threshold, it is determined that the user is simply a passenger, or a driver of the vehicle in an autonomous driving mode at a level higher than or equal to 80%.

As indicated above by way of example, the aforementioned notification signal may be transmitted to a communication apparatus of the user. This communication apparatus may be a smartphone, tablet computer, PC, etc., which is typically connected to a cellular network. The notification signal may be received via this network, by SMS, instant messaging or e-mail, respectively.

In this form of embodiment, the communication apparatus may be configured to determine whether the user is in a moving vehicle, and in this case, filter incoming notifications to be delivered to the communication apparatus. The method further determines whether the user is not in an active driving situation, and in this case deactiveates filtering of incoming notifications to be delivered to the communication apparatus.

What is meant here by "filtering incoming notifications" is equally well, i.e. without distinction, the ability to cut the communication apparatus off from the cellular network so as to prevent the reception of any notifications (for example as in "airplane" mode), as the ability to receive notifications but not display them on the device screen.

For example, the apparatus may comprise a module for detecting motion of the device (for example via geolocation, etc.) and thus determining, above a threshold speed, that the user is in a moving vehicle. In this case, this detector module may filter all incoming notifications to be delivered to the device, but may also communicate with a processing circuit located on-board the vehicle and connected to the eye-movement sensor, in order to let notifications be delivered to the apparatus if the processing circuit determines that the user is not in an active driving situation.

In addition or as a variant, the method may further determine a current position of the vehicle, and trigger, depending on the current position of the vehicle, relevant notification signals intended for the device of the user.

For example, the vehicle may comprise a module for determining current position (GPS module, GPS standing for Global Positioning System), and a processing circuit connected, on the one hand to the eye-movement sensor, with a view to implementing the above method, and on the other hand to the aforementioned module for determining current position, with a view to determining a current position of the vehicle and to triggering, depending on the current position of the vehicle, relevant notification signals intended for the apparatus of the user.

It is thus possible to offer a "guided tour" of the landscape to the user during the user's journey in the vehicle.

In one embodiment, the sensor device may further measure an amplitude of eye movements of the user, and the method then further compares a current amplitude with a threshold amplitude, and if the current amplitude is lower than the threshold amplitude, determining that the user is suffering from an episode of motion sickness, and triggering an action in the vehicle to provide relief to the user.

Specifically, it has been observed that a lower user movement amplitude is correlated with the user experiencing motion sickness.

Once again, the method may employ artificial intelligence to detect, specifically for this user, motion sickness or a risk of motion sickness, the method feeds an artificial intelligence with data generated by the sensor device with a view to recognizing at least one eye-movement amplitude of the user, the user having an episode of motion sickness when the measured eye-movement amplitude is lower than said threshold amplitude.

The action that may be triggered in the vehicle may include decreasing the speed of the vehicle at least in bends that the vehicle takes, spraying scents into the passenger compartment of the vehicle, modifying the thermal conditions in the passenger compartment, projecting a light scenario into the passenger compartment.

In one embodiment, the method may further include obtaining current geolocation coordinates of the vehicle with a view to identifying a current route of the vehicle as being a risk factor for onset of motion sickness, and transmitting the current geolocation coordinates to a database server with a motion-sickness identifier.

In this embodiment, the remote server is preferably capable of receiving geolocation coordinates from a fleet of vehicles, with a motion-sickness identifier, estimating for a plurality of possible routes from one point to another, respective motion-sickness-onset-risk scores, and transmitting, to one or more vehicles, data with a view to determining an alternative route to a route with a high motion-sickness-onset-risk score.

Communication with the server may be ensured via the communication apparatus (smartphone, etc.) of the user or via a cellular communication module installed in the vehicle.

It is further possible to provide an accelerometer (in the vehicle, for example in the smartphone of the user) with a view to estimating a current vehicle-jolt frequency, a route being confirmed a motion-sickness-onset risk if the current jolt frequency exceeds a threshold frequency.

In one embodiment, provision may further be made for a UV-radiation sensor (UV standing for ultraviolet) and, in case of detection of a UV-radiation signature higher than a radiation threshold, said notification intended for the user comprises a message raising consciousness of UV radiation.

In addition to this notification, it is possible to trigger an action in the vehicle in case of detection of UV radiation, among at least: the action of a nebulizer, ventilation, air-conditioning, opacification to UV rays of the windows of the vehicle.

Moreover, the UV-radiation sensor may be a sensor of light intensity at UV wavelengths or simply a sensor of temperature difference due to solar radiation in the passenger compartment.

The present invention also relates to a device comprising a processing circuit and at least one eye-movement sensor of the aforementioned type for implementing the above method.

In such a device, the eye-movement sensor device for sensing eye movements of the user may be mounted on a connected pair of glasses worn by the user (as illustrated in FIG. 1, which is described below). This pair of glasses may also bear the aforementioned accelerometer, the UV-radiation detector, and/or other things, or even also the communication apparatus if said glasses are smartglasses with the lenses of which may be used to display information.

As a variant, the eye-movement sensor device for sensing eye movements of the user may be mounted on a camera arranged in the passenger compartment of the vehicle (facing the driver for example), the camera being able to be connected to an eye tracker module in order to detect the frequency (and optionally the amplitude) of the eye movements of the user. A so-called driver monitoring system (DMS), which potentially already exists in the vehicle and which in particular serves to detect if the driver is falling asleep, may be equipped with such an interior camera, for example.

The present invention also relates to a computer program comprising instructions for implementing the above method, when these instructions are executed by a processor. It also relates, equivalently, to a non-volatile storage medium able to durably (or not) store such a computer program.

BRIEF DESCRIPTION OF THE DRAWINGS

Further features, details and advantages will become apparent on reading the following detailed description, and on studying the appended drawings, in which.

DETAILED DESCRIPTION OF THE INVENTION

The drawings and the description below contain, for the most part, elements of a certain character. Therefore, they may not only be used to better understand the present disclosure, but also contribute to its definition, where appropriate.

Figure 1:
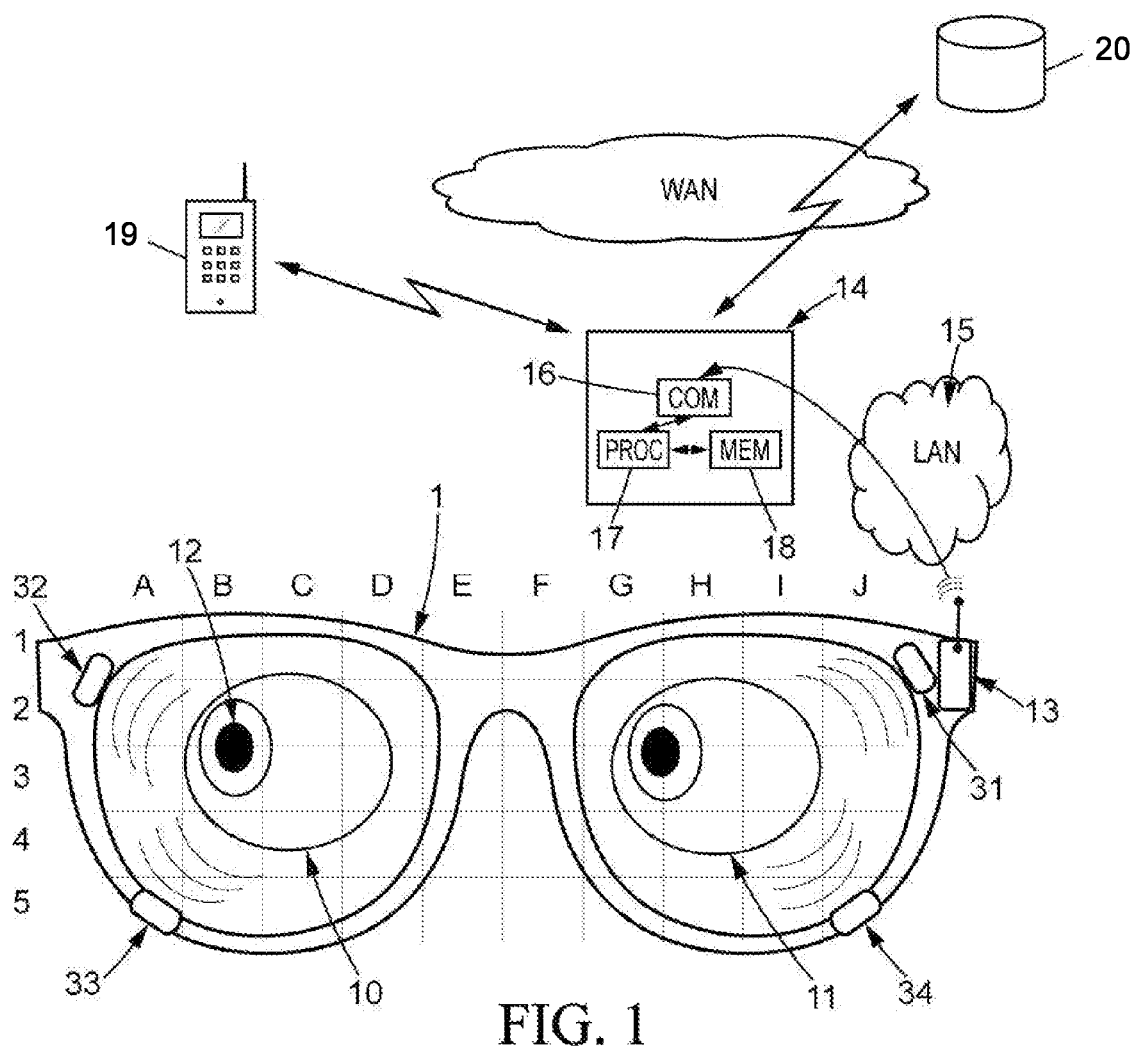
FIG. 1 shows a schematic of a system for detecting a state regarding whether a user in a motor-vehicle passenger compartment is actively driving or not according to one embodiment of the invention.

With reference to FIG. 1, a device for detecting a state of a passenger in a motor vehicle regarding whether a user is actively driving the vehicle or not will first be described.

The device comprises a plurality of sensors 31, 32, 33, 34 installed, in the described example, in the frame 1 of a connected pair of glasses. Specifically, these sensors are connected to a communication module 13 installed in the frame and capable of sending measurement signals taken by these sensors to a processing circuit 14 that the device also comprises. In particular, the sensor 31 is a first camera able to track eye movement (here of the right eye 11 of the user), and the sensor 32 is a second camera able to track the eye movement of the left eye 10 of the user. In particular, these cameras 31, 32 and the processing circuit 14 are together capable of measuring a movement of the retina of each eye of the user relative to the setting formed by the periphery of the eye. For the sake of illustration, FIG. 1 shows the periphery of the left eye 10, the periphery of the right eye 11, and the position of the left pupil 12 within a grid indexed A to J column-wise and 1 to 5 row-wise. The position of the right pupil has also been shown. The grid is a virtual division of the area through which the pupils travel when they are in motion.

The sensors 31, 32 may for example operate in the infrared and may each comprise an infrared light-emitting diode and an infrared photodetector. The infrared light-emitting diode is selected that is harmless to human vision. The infrared light-emitting diode is configured to emit an infrared beam in the direction of the pupil of one of the two eyes, and the infrared photodetector is able to detect a reflection of the infrared beam from the cornea of the eye.

Of course, as a simplified variant, a single camera targeted at a single eye of the user may be provided. Furthermore, alternatively to mounting on a pair of connected glasses, the camera may be mounted in the passenger compartment for example in the context of DMS surveillance as indicated above.

The processing circuit 14 comprises a communication interface 16, in particular for communicating with the module 13 (via for example a local-area network 15), as well as a processor 17 and a working memory 18 that interacts with the processor 17. The processing circuit 14 is then configured to determine the position of the pupil in the virtual grid on the basis of the intensity and of the spectrum of the infrared beams reflected and captured by each of the photodetectors. The processing circuit 14 is further configured to timestamp the positions of the pupils as they are captured. To do this, the processing circuit (and more particularly its processor 17) may further comprise a clock or means for accessing external clock data (not shown).

Alternatively to communication between the module 13 and the processing circuit 14 via for example a local-area network 15 in the passenger compartment, the processing circuit 14 may be directly installed in the frame 1 and be connected directly to the sensors 31 to 34. On the other hand, in the illustrated example, the communication interface 16 of the processing circuit 14 is preferably connected, directly or indirectly (via the local-area network 15 or via a wide-area network WAN), to a communication apparatus 19 (a smartphone, etc.) available to the user, in particular with a view to filtering or not notifications intended for the user. Furthermore, in the example shown, the communication interface 16 of the processing circuit 14 is connected, preferably via the wide-area network WAN, to a remote server 20 which keeps up to date information on rough routes and in particular routes likely to give passengers motion sickness. To this end, this server may comprise at least one communication interface and one storage memory (not shown).

Furthermore, the connected frame 1 may also comprise an accelerometer-type sensor 33 for confirming that a route in the process of being travelled is rough, as detailed below, this sensor also being connected to the processing circuit 14 (possibly via the communication module 13). Furthermore, the connected frame 1 may also comprise a sensor 34 for detecting UV radiation, with a view to comparing current radiation with a threshold and to triggering an action if the current radiation is higher than the threshold. The sensor 34 can also be connected to the processing circuit 14 (possibly via the communication module 13).

Figure 2:
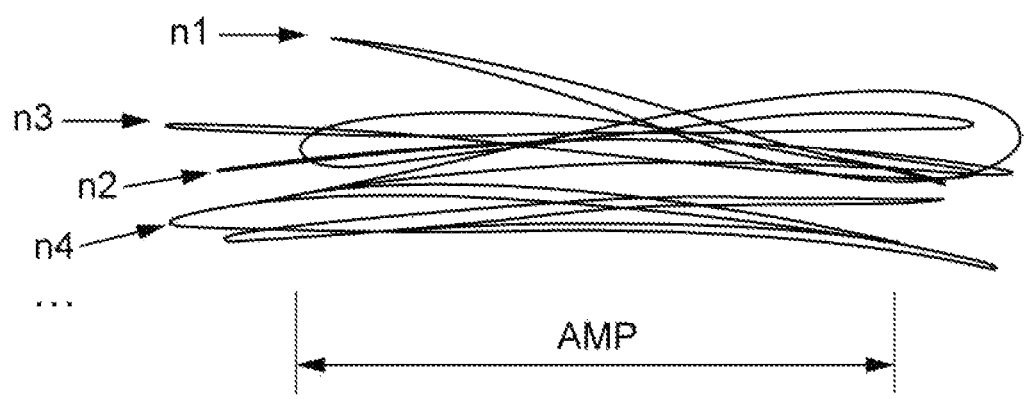
FIG. 2 very schematically shows an eye movement of a user according to one embodiment of the invention.

FIG. 2 illustrates eye movements over time and in particular back-and-forth excursions n1, n2, n3, n4 etc. of the pupil of the eye, these back-and-forth excursions being characteristic of a passenger watching a landscape passing by, and not being fixedly focused on the road as an active driver of the vehicle would be. Moreover, the movements are on average horizontal (or deviate little from a substantially horizontal line) and have a higher average amplitude (AMP) than a habitual eye-movement amplitude of an active vehicle driver. Thus, the processing circuit 14 is programmed at least to count the number of back-and-forth excursions n1, n2, etc. per unit time (e.g. in one minute) that have significant amplitude (AMP), and to deduce therefrom a frequency (Freq) of these characteristic eye movements.

Figure 3:
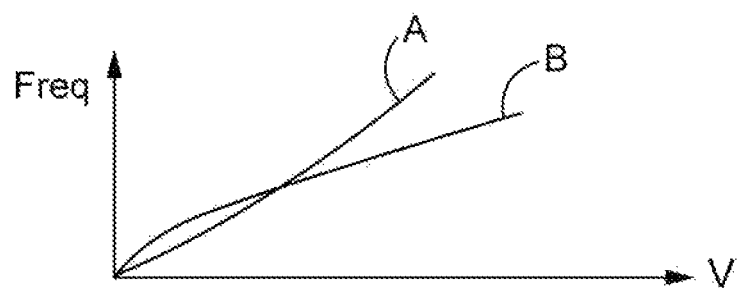
FIG. 3 schematically compares the eye-movement frequencies (here as a function of vehicle speed) of two different users A and B according to one embodiment of the invention.

This frequency (Freq) may vary in particular as a function of the current speed (V) of the motor vehicle. However, the data, such as frequency (Freq) and amplitude (AMP), are, critically, unique to each individual. For purely illustrative purposes, a variation (here as a function of the speed (V) of the vehicle) in the frequency (Freq) of eye movements for two respective individuals A and B has been shown in FIG. 3.

Figure 4:
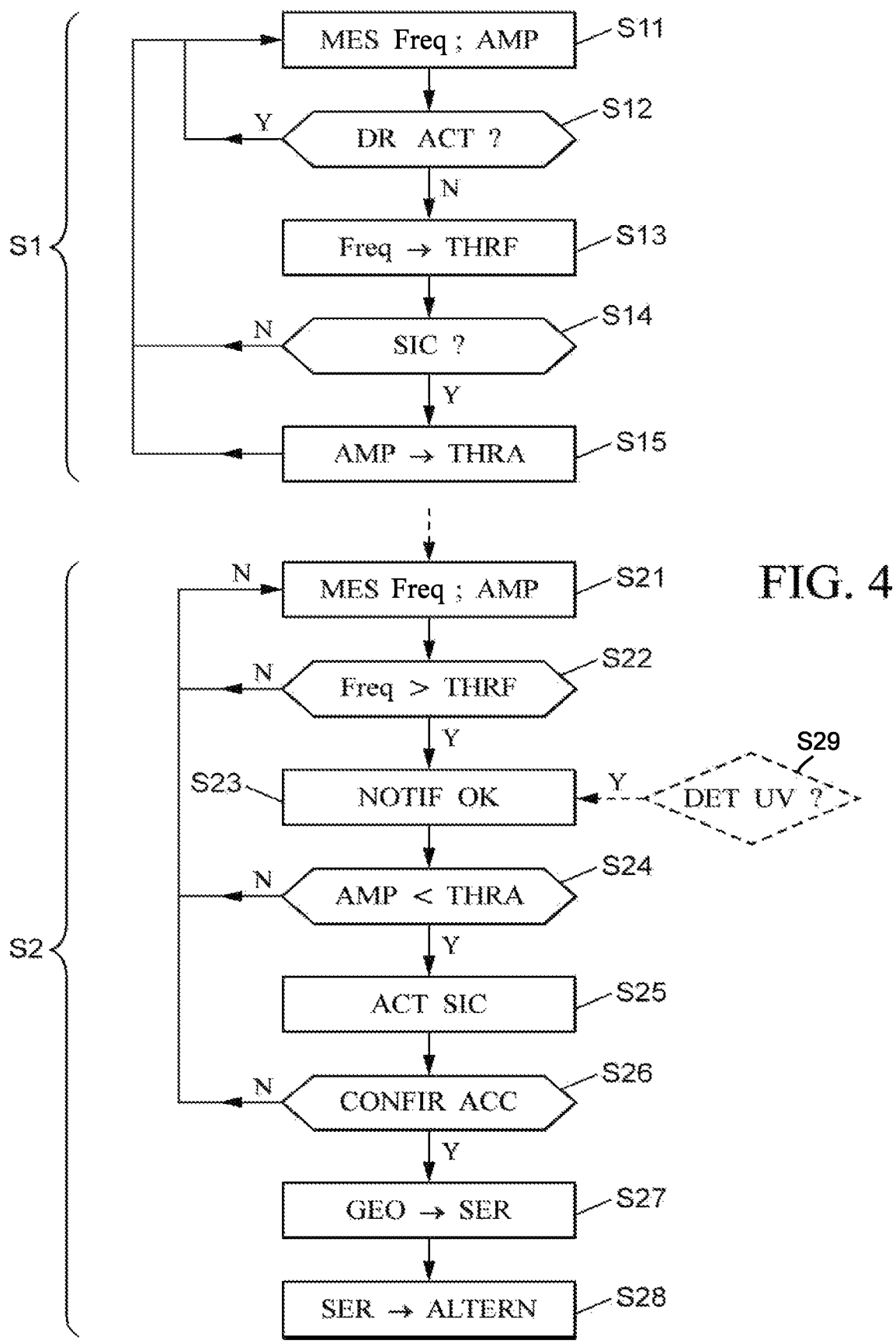
FIG. 4 shows a method for detecting a state regarding whether a user in a motor-vehicle passenger compartment is actively driving or not according to one embodiment of the invention.

Thus, with reference now to FIG. 4, a first general step S1 is provided in which parameters characteristic of the user, such as the frequency (Freq) (in particular as a function of the speed (V)) and the average amplitude (AMP), are learnt by an artificial intelligence (for example a neural network, a deep neural network for example). Specifically, by way of non-limiting examples, the artificial intelligence may employ deep learning, a trained neural network, or machine learning. A "neural network" may generally be defined by a set of transfer functions the coefficients of which are gradually modified (as training progresses) depending on a newly acquired succession of time-stamped pupil positions that is labelled as being characteristic of a scenario to be recognized.

This general learning step S1 thus precedes an everyday use S2 of the artificial intelligence to detect an active (actual) driving state of the user and potentially whether the user is suffering from motion sickness.

Thus, a first step S11 consists in employing the sensors 31 and 32 to repeatedly measure the amplitude (AMP) of eye movements of a given user and their frequency (Freq) (as a function of the speed (V) of the vehicle for example). These measurements are labelled (or tagged) by an identifier in a database depending on a real, i.e. actual, situation of the user. It may typically be indicated whether the user is (output Y of step S12) or is not in an active driving state. Typically, if the user is not in an active driving state (output N of step S12), the user's eye-movement frequency may be determined in step S13, and steps S11 to S13 are carried out repeatedly until a minimum average frequency threshold (THRF), above which the user is definitely in a state in which the user is not actively driving the vehicle (simply a passenger or vehicle in a driving mode that is more that 80% autonomous), has been determined. The user is further asked, in step S14, whether the user is experiencing motion sickness (repeatedly) and if so (output Y of test S14), the current measurement of eye-movement amplitude may be tagged in the training database, in step S15, as being a minimum amplitude threshold (THRA) below which the user begins to experience motion sickness. Specifically, it has been observed that an eye-movement amplitude below a threshold but nevertheless characteristic of a person watching the landscape pass by is generally correlated with this person having motion sickness.

Of course, these steps are repeated a plurality of times to keep up to date the frequency threshold (THRF) and amplitude threshold (THRA) specific to the user (above which (THRF) the user is not in an active driving state, and below which (THRA) the user begins to experience motion sickness, respectively).

Reference will now be made to the second general step S2 of FIG. 4, to describe an everyday implementation of the method, once the frequency and amplitude thresholds (THRF, THRA) have been determined for a given user.

In step S21, the current frequency of the eye movements of this user and their amplitude are measured.

In step S22, if this frequency is higher than the threshold (THRF) (arrow Y exiting the test S22), then it may be determined with certainty that the user is not in an active driving state and it is thus possible, in step S23, to send the user notifications via for example the user's communication apparatus 19 (smartphone, etc.). Thus, if the communication apparatus 19 comprises a computing module that is able to detect a state of mobility the speed of which is higher than a threshold (this meaning that the user is in a moving vehicle and that the user is likely to be driving this vehicle), and then to block any incoming notification (for the sake of safety), in step S23, it is possible to deactivate this module of the smartphone and thus to permit the latter to receive and display incoming notifications.

For example, one possible incoming notification may consist of an alert regarding a level of UV radiation inside the passenger compartment detected to be excessive by the sensor 34 in step S29 (arrow Y exiting test S29). In this case and as described above, provision may be made to take a specific action in the passenger compartment, such as for example spraying nebulized water in the direction of the user, etc.

Moreover and optionally, the amplitude of the eye movements of the user may be tracked with a view to determining whether it has dropped below a threshold (THRA) determined in the general step S1, this meaning that the user is detected in step S24 to be suffering from motion sickness. In this case (arrow Y exiting the test S24), provision is made to trigger an action in the passenger compartment in step S25 to provide relief to the user. It may typically be a question of slowing down of the pace of the vehicle, in particular in bends (in case of autonomous driving), modifying the thermal conditions in the passenger compartment for the user, spraying specific scents that may provide the user relief, projecting a hologram to attract the attention of the user, etc.

Optionally, the accelerometer-type sensor 33 may confirm the presence of jolts experienced by the user in the vehicle, in step S26. In this case, data regarding the current geolocation of the vehicle may be transmitted, in step S27, to the server 20 introduced above with reference to FIG. 1, with a view to storing this current geolocation (or more generally the route that the vehicle is in the process of travelling) with a motion-sickness-risk identifier. This data regarding current geolocation may be determined by a GPS chip that the processing circuit 14 may comprise, or may alternatively be obtained by communication with the communication apparatus 19 of the user (which usually comprises a means for obtaining a geolocation data via a GPS chip or via triangulation in the cellular network). This identifier may make it possible to score the route with a motion-sickness-risk score that may be dependent on the frequency of the detected jolts and/or on their amplitude.

Optionally, the processing circuit 14 (for example via the communication apparatus 19) may then make a request to the server 20 in step S28 with a view to obtaining an alternative route that may then be displayed on a screen of a navigation device, etc., connected to the processing circuit 14.

Of course, the present invention is not limited to the embodiments described above by way of example; it encompasses other variants.

For example, a method in which artificial intelligence allows a specific signature of the eye movements of an individual who is not in an active driving state to be defined was described above. Of course, it is possible to first define an average signature of a panel of users (in a first general step S1) and then to apply it, in an everyday step S2, to a given user. Moreover, it is possible to refine the signature of the eye movements of a given individual by confirming, during the everyday step S2, that the user is or is not actually in an active driving state. By way of example, a notification may be transmitted to any screen in the passenger compartment of the vehicle or to the smartphone of the user, and if the user does not respond to it, it is concluded that the user is actually in an active driving state.

Moreover, the sensors 31 to 34 may be grouped together on a frame of a pair of connected glasses as described above, or alternatively be dispersed through the passenger compartment of the vehicle while nevertheless being connected to the processing circuit 14.

What is claimed is:

1. A method for determining at least one state of a user in a motor-vehicle passenger compartment, regarding whether is the user is actively driving the vehicle or not,
with an eye-movement sensor device for sensing eye movements of the user, the method comprising:
updating an artificial intelligence with eye-movement frequency data generated by the sensor device for the user, with an eye-movement frequency above a first threshold being characteristic of the user viewing a landscape passing by, and being distinguishable from the eye-movement frequency of a concentrated gaze of a vehicle driver,
determining a current eye-movement frequency of the user from the eye-movement frequency data, comparing the current frequency with the first threshold, and triggering a notification signal intended for the user when the current frequency is greater that the first threshold.

2. The method as claimed in claim 1, wherein the current frequency greater than the first threshold determines that the user is simply a passenger, or a driver of the vehicle in an autonomous driving mode at a level higher than or equal to 80%.

3. The method as claimed in claim 1, further comprising transmitting the notification signal to a communication apparatus of the user.

4. The method as claimed in claim 3, wherein the communication apparatus is configured to filter incoming notifications to be delivered to the communication apparatus when the communication apparatus determines the user is in a moving vehicle, with the method further comprising:

determining a status of whether the user is not in an active driving situation, and transmitting the status to the communication apparatus in order for the communication apparatus to deactivate filtering of incoming notifications to be delivered to the communication apparatus when the user is not in an active driving situation.

5. The method as claimed in claim 3, further comprising:

determining a current position of the vehicle, and triggering relevant notification signals intended for the communication apparatus responsive to the current positon of the vehicle.

6. The method as claimed in claim 1, wherein the sensor device further measures an eye-movement amplitude, and the method further comprises:

comparing a current amplitude with a threshold amplitude, and determining that the user is suffering from an episode of motion sickness if the current amplitude is lower than the threshold amplitude, and triggering an action in the vehicle to provide relief to the user.

7. The method as claimed in claim 6, further comprising:

updating the artificial intelligence with amplitude data generated by the sensor device of the user when the user has the episode of motion sickness.

8. The method as claimed in claim 6, wherein the action in the vehicle includes at least one of decreasing the speed of the vehicle at least in bends that the vehicle takes, spraying scents into the passenger compartment of the vehicle, modifying the thermal conditions in the passenger compartment, or projecting a light scenario into the passenger compartment.

9. The method as claimed in claim 6, further comprising:

obtaining current geolocation coordinates of the vehicle in order to identify a current route of the vehicle as a risk factor for onset of motion sickness, and transmitting the current geolocation coordinates to a database server with a motion-sickness identifier.

10. The method as claimed in claim 9, wherein the database server is capable of:

receiving geolocation coordinates from a fleet of vehicles, with a motion-sickness identifier, estimating, for a plurality of possible routes from one point to another, respective motion-sickness-onset-risk scores, and transmitting, to one or more vehicles, data in order to determine an alternative route for a current route with a high motion-sickness-onset-risk score.

11. The method as claimed in claim 9, further comprising estimating a current vehicle jolt frequency with an accelerometer, and confirming the current route is a motion-sickness-onset risk when the current jolt frequency exceeds a threshold frequency.

12. The method as claimed in claim 1, further comprising notifying the user with a message raising consciousness of UV radiation when a UV-radiation sensor detects a UV-radiation signature higher than a radiation threshold.

13. A device comprising:

at least one eye-movement sensor; and a processing circuit connected to the at least one eye-movement sensor, the processing circuit configured to update an artificial intelligence with eye-movement frequency data generated by the at least one eye-movement, with an eye-movement frequency above a first threshold being characteristic of a user viewing a landscape passing by, and being distinguishable from the eye-movement frequency of a concentrated gaze of a vehicle driver, determine a current eye-movement frequency of the user from the eye-movement frequency data, compare the current frequency with the first threshold, and trigger a notification signal intended for the user when the current frequency is greater that the first threshold.

14. The device as claimed in claim 13, wherein the eye-movement sensor is included in a connected pair of glasses worn by the user.

15. The device as claimed in claim 13, wherein the eye-movement sensor is included in a camera arranged in the passenger compartment of a vehicle.

* * * * *